US00PP30564P3

(12) United States Plant Patent
Whitaker

(10) Patent No.: US PP30,564 P3
(45) Date of Patent: Jun. 11, 2019

(54) STRAWBERRY PLANT NAMED 'FLORIDA BRILLIANCE'

(50) Latin Name: ***Fragaria* X *ananassa* Duchesne**
Varietal Denomination: Florida Brilliance

(71) Applicant: Florida Foundation Seed Producers, Inc., Marianna, FL (US)

(72) Inventor: Vance M. Whitaker, Brandon, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 15/732,323

(22) Filed: Oct. 24, 2017

(65) Prior Publication Data

US 2019/0124811 P1 Apr. 25, 2019

(51) Int. Cl.
*A01H 5/08* (2018.01)

(52) U.S. Cl.
USPC ..... Plt./208
CPC ..... *A01H 5/08* (2013.01)

(58) Field of Classification Search
USPC ..... Plt./208, 209
CPC ..... A01H 5/0893
See application file for complete search history.

(56) References Cited

U.S. PATENT DOCUMENTS

PP20,363 P2 9/2009 Chandler
PP25,574 P3 5/2015 Whitaker et al.

*Primary Examiner* — Kent L Bell
(74) *Attorney, Agent, or Firm* — Dentons US LLP

(57) ABSTRACT

A new and distinct variety of strawberry (*Fragaria* X *ananassa*), which originated from seed produced by a hand-pollinated cross between 'FL 11.31-14' and 'FL 10-153'. The new strawberry, named 'Florida Brilliance', can be distinguished at least by its high early and total yields; exceptional fruit shape and firmness; and balanced flavor when grown in West Central Florida or other regions that have a climate similar to that of West Central Florida.

1 Drawing Sheet

Latin name of the genus and species of the plant claimed: *Fragaria* X *ananassa* Duchesne.

Variety denomination: 'Florida Brilliance'.

BACKGROUND OF THE INVENTION

The present invention relates to a new and distinct variety of strawberry plant (*Fragaria* X *ananassa* Duchesne) named 'Florida Brilliance'. This new strawberry plant is distinguished at least by its ability to produce high early and total yields of fruit that are consistently shaped, have exceptional firmness, and have good flavor when grown in West Central Florida. Asexual propagation of 'Florida Brilliance' was performed at Balm, Fla., which is also where the selection was made and the plants were tested. 'Florida Brilliance' can be contrasted with 'Florida Radiance' (U.S. Plant Pat. No. 20,363) and 'Florida127' (U.S. Plant Pat. No. 25,574), which are the current, dominant strawberry varieties in Hillsborough County, Fla. 'Florida Brilliance' is a promising candidate for commercial success because it produces higher yields in November and December when market prices are high and because it produces firm, evenly colored, and consistently shaped fruit throughout the entire Florida market window.

SUMMARY OF THE INVENTION

'Florida Brilliance', when grown in a subtropical climate during the fall, winter, or a combination thereof, can be distinguished from all other strawberry plants by at least the following characteristics: high early and total fruit yield; exceptionally firm fruit; consistently well-shaped fruit; bright medium-red fruit; and fruit with a balanced flavor.

'Florida Brilliance' originated in a strawberry breeding plot in Balm, Fla. The seed parent was 'FL 11.31-14', an unreleased, unpatented breeding selection with excellent fruit size and disease resistance. The pollen parent was 'FL 10-153', an unreleased, unpatented breeding selection with high early yields, excellent fruit shape, and compact plant. The seeds resulting from the controlled hybridization were germinated in a greenhouse, and the resulting seedlings were planted and allowed to produce daughter plants by asexual propagation (i.e. by runners). Two daughter plants from each seedling were transplanted to raised beds, where they fruited. 'Florida Brilliance' was selection number 134 of the $26^{th}$ cross in the 2013-2014 seedling trial, and thus was given the breeding trial designation of 'FL 13.26-134'. 'Florida Brilliance' exhibited high early and total yields of consistently shaped fruit. 'Florida Brilliance' has been asexually propagated annually by runners; and test plantings have established that the vegetative and fruit characteristics of the propagules are identical to those of the initial daughter plants.

'Florida Brilliance' can be distinguished from its seed parent 'FL 11.31-14' at least by its more consistent fruit shape, better fruit flavor, greater early yields, and more compact plant habit. 'Florida Brilliance' can also be distinguished from its pollen parent 'FL 10-153' at least by its larger fruit size, more upright plant architecture, and greater disease resistance.

Currently, 'Florida Radiance' (U.S. Plant Pat. No. 20,363) and 'Florida127' (U.S. Plant Pat. No. 25,574) are the two dominant strawberries varieties in Hillsborough County, Fla.

The fruit of 'Florida Brilliance' are similar in flavor to those of 'Florida Radiance', but 'Florida Brilliance' fruit are larger than those of 'Florida Radiance' in some seasons (see Table 1) and are firmer than the fruit produced by either 'Florida Radiance' or 'Florida127', see Table 2. The fruit of 'Florida Brilliance' are also more resistant to rain damage than the fruit of 'Florida127'. Furthermore, 'Florida Brilliance' has more consistent conical fruit shape and achieves higher fruit yield in November than either 'Florida Radiance' or 'Florida127', see Table 1.

'Florida Brilliance' is also expected to perform better in nurseries than 'Florida Radiance'. 'Florida Brilliance' runners produce daughter plants that are sturdier and more compact than those produced by 'Florida Radiance' runners. Also, 'Florida Brilliance' is resistant to powdery mildew (caused by *Podosphaera aphanis*), like 'Florida Radiance', but is also highly resistant to anthracnose fruit rot (caused by *Colletotrichum acutatum*) and charcoal rot (caused by *Macrophomina phaseolina*), like 'Florida127'.

BRIEF DESCRIPTION OF THE DRAWINGS

'Florida Brilliance' is illustrated by the accompanying photograph that shows 1.5-month-old specimens. The colors shown are as true as can be reasonably captured by conventional photographic procedures. The photograph was captured in December of 2016 in West Central Florida.

FIG. 1. Shows 1.5-month-old whole plants, including foliage, inflorescences, and fruit at varying stages of ripeness.

DETAILED BOTANICAL DESCRIPTION

The following detailed botanical description sets forth the distinctive characteristics of 'Florida Brilliance'. The present botanical description is of 'Florida Brilliance' when grown under the ecological conditions that prevail during the winter production season in Balm, Fla., i.e., warm days and cool nights. Colors are objectively described using the L*a*b* color scale as measured with a colorimeter.

PHENOTYPIC DESCRIPTION OF *FRAGARIA* X *ANANASSA* DUCHESNE 'FLORIDA BRILLIANCE'

Classification:
- *Botanical.*—*Fragaria* X *ananassa* Duchesne.
- *Common name.*—Strawberry.

Parentage:
- *Seed parent.*—'FL 11.31-14'.
- *Pollen parent.*—'FL 10-153'.

Plant:
- *Average height.*—18 cm to 20 cm.
- *Average width.*—27 cm to 30 cm.
- *Growth habit.*—Compact, semi-upright and not overly dense.
- *Number of crowns per plant.*—4 to 7 depending on seasonal conditions.
- *Vigor.*—Medium.

Leaf:
- *Overall description.*—Pinnately compound with three leaflets.

Petiole:
- *Average length.*—15.5 cm.
- *Average diameter.*—2.5 mm to 3.0 mm.
- *Pubescence.*—Light.
- *Pubescence density.*—Sparse.
- *Pose of hairs.*—Perpendicular.
- *Texture.*—Smooth.
- *Anthocyanin presence.*—Absent.
- *Color.*—Medium-light green (L*=55.91, a*=−16.05, b*=32.58).

Petiolule:
- *Length.*—Terminal leaflet: 12 mm. Lateral leaflets: 10 mm.
- *Diameter.*—2 mm.
- *Color.*—Medium-light green (L*=65.21, a*=−13.44, b*=28.51).

Stipule:
- *Length.*—33 mm to 35 mm.
- *Width.*—20 mm along the base of the petiole attachment.
- *Anthocyanin presence.*—Occasional.
- *Color.*—Light green (L*=72.72, a*=−13.48, b*=35.37).

Terminal leaflet:
- *Average length.*—99 mm.
- *Average breadth.*—91 mm.
- *Length/width ratio.*—1.09.
- *Shape in cross section.*—Concave.
- *Color, upper surface.*—Medium-light green (L*=35.6, a*=−13.9, b*=17.8).
- *Color, lower surface.*—Light green (L*=51.07, a*=−13.35, b*=19.0).
- *Glossiness.*—Slight gloss.
- *Base shape.*—Cuneate.
- *Apex descriptor.*—Rounded.
- *Pubescence density.*—Sparse.
- *Texture.*—Moderately smooth.
- *Venation pattern.*—Pinnate.

Secondary leaflets:
- *Average length.*—88 mm.
- *Average breadth.*—81 mm.
- *Length/width ratio.*—1.08.
- *Shape in cross section.*—Concave.
- *Color, upper surface.*—Medium-light green (L*=36.1, a*=−12.8, b*=16.2).
- *Color, lower surface.*—Light green (L*=50.38, a*=−13.79, b*=20.36).
- *Glossiness.*—Slight gloss.
- *Base shape.*—Oblique rounded.
- *Apex descriptor.*—Obtuse.
- *Pubescence density.*—Sparse.
- *Texture.*—Moderately smooth.
- *Venation pattern.*—Pinnate.

Leaflet margins: Crenate, with an average of 22 and 21 serrations per terminal and secondary leaflet, respectively.

Stolons:
- *Number of daughter plants.*—20 to 40 depending on environmental conditions.
- *Anthocyanin presence.*—Occasional.
- *Thickness.*—2 mm to 3 mm.
- *Pubescence.*—Light.

Inflorescence:
- *Time of flowering.*—Partial remontancy, commencing two weeks after establishment and continually thereafter in suitable climate.
- *Flower number per plant.*—45 to 60 flowers over a 4 month Florida growing season.
- *Flower height.*—0 to 30 cm above soil surface depending on angle of pedicel.

*Position relative to canopy*.—Flowers open at or below canopy height.

*Branching of the inflorescence*.—At or very close to the crown.

Petals:

*Number*.—6 to 8.

*Length*.—11 to 14 mm.

*Width*.—12 to 14 mm.

*Shape*.—Orbicular.

*Apex*.—Rounded.

*Base*.—Rounded.

*Margin*.—Smooth.

*Average diameter of the corolla* (*i.e. the petals collectively*).—32 mm.

*Average number of stamens*.—29.

Calyx:

*Diameter*.—40-50 mm.

*Diameter of calyx relative to corolla*.—60% greater in diameter.

*Diameter of calyx relative to the fruit*.—0-10% greater in diameter.

*Insertion of calyx*.—Level to slightly inserted.

*Color*.—Medium green (L*=37.7, a*=−14.4, b*=18.8).

Sepals:

*Number per flower*.—14-15.

*Length*.—10-20 mm.

*Width*.—5-10 mm.

*Apex*.—Subacute to lobed.

*Margin*.—Smooth.

*Color, upper surface*.—Medium green (L*=42.73, a*=−18.9, b*=25.72).

*Color, lower surface*.—Light green (L*=53.77, a*=−15.59, b*=22.59).

Pedicels: Attached to mature primary fruit and 10 cm to 14 cm in length and 1.5 to 2.0 mm in diameter depending on the time of the season. At peak production, the plant will have several crowns, each producing a truss. Each truss will have 5 to 8 pedicels. Inflorescences branch very close to the crown, rendering the peduncle rarely visible.

Fruit:

*Average fruit weight*.—20.2 g to 20.7 g.

*Number per truss*.—5 to 8.

*Shape*.—Medium conical to cordate.

*Weight, primary fruit*.—25 g to 40 g.

*Weight, secondary and tertiary fruit*.—15 g to 25 g.

*Length, primary fruit*.—45 to 55 mm.

*Width, primary fruit*.—35 to 45 mm.

*Fruit flavor*.—Similar to 'Florida Radiance', which is the current commercial standard in Florida, see Table 2.

*Fruit soluble solids content* (*brix*).—8.5% in February 2016.

*Fruit firmness*.—Higher than either 'Florida127' or 'Florida Radiance' in sensory tests, see Table 2.

*Fruit cavity*.—Rare.

*Achenes*.—Sunken, which gives the fruit a glossy appearance, 120 to 300 per fruit.

*External fruit color*.—Glossy medium red (a*=34.7).

*Internal fruit color*.—Medium red (a*=22.7).

*Evenness of color*.—Consistently even.

*Flesh and skin firmness at full ripe stage*.—Very firm.

*Rain damage*.—More resistant to cracking of the fruit by rain than 'Florida127' and similar to 'Florida Radiance'.

Early yield: Higher November yields than 'Florida127' in 2015-2016 and both 'Florida127' and 'Florida Radiance' in 2016-2017, see Table 1.

Preferred planting period: October 1$^{st}$ to October 15$^{th}$ in West Central Florida.

Nursery performance: 'Florida Brilliance' is expected to perform well in nursery situations due to the production of a moderate to high number of runners that result in sturdy, compact daughter plants. This is in contrast to 'Florida Radiance', whose daughter plants have weak petioles that are susceptible to breakage during digging and handling.

Disease resistance:

*Botrytis fruit rot* (*caused by botrytis cinerea*).—Moderately susceptible.

*Powdery mildew* (*caused by podosphaera aphanis*).—Resistant.

*Anthracnose fruit rot* (*caused by colletotrichum acutatum*).—Highly resistant.

*Charcoal rot* (*caused by macrophomina phaseolina*).—Highly resistant.

TABLE 1

Performance of three strawberry genotypes during the 2015-2016 and 2016-2017 seasons in Balm, Florida.

| | Marketable yield (g/plant) | | | |
|---|---|---|---|---|
| Cultivar | November | December | January | February |
| 2015-16 | | | | |
| 'Florida Brilliance' | 70.0 a[y] | 132.1 a | 49.8 a | 177.0 a |
| 'Florida127' | 39.6 b | 75.3 b | 38.2 a | 129.4 a |
| 2016-17 | | | | |
| 'Florida Brilliance' | 30.3 a | 125.3 a | 154.8 b | 452.1 a |
| 'Florida127' | 14.1 b | 115.2 a | 211.9 a | 428.7 a |
| 'Florida Radiance' | 6.3 b | 102.3 a | 157.2 b | 413.9 a |

| | Marketable yield (g/plant) | | |
|---|---|---|---|
| Cultivar | March | Total | Wt/fruit (g)[z] |
| 2015-16 | | | |
| 'Florida Brilliance' | 209.6 a | 638.6 a | 20.2 b |
| 'Florida127' | 129.4 b | 411.9 a | 21.5 a |
| 2016-17 | | | |
| 'Florida Brilliance' | 251.9 a | 1014.4 a | 20.7 b |
| 'Florida127' | 197.1 b | 967.0 ab | 23.5 a |
| 'Florida Radiance' | 174.1 b | 853.8 b | 18.8 c |

[z]Mean fruit weight was determined by dividing total marketable fruit yield per plot by total marketable fruit number per plot.

[y]Means are based on four replications of 10 plants each in 2014-2015 and on five replications of 10 plants each in the other seasons. Means separation within columns is by Tukey's HSD test, $P \leq 0.05$. Different letters within column and within season indicate comparisons that achieved statistical significance.

Yield data for 'Florida Radiance' was not available in 2015-2016.

TABLE 2

Trained sensory panel ratings from five dates over two harvest seasons.

| Cultivar | Firmness | Sweetness | Sourness | Strawberry flavor | Green flavor |
|---|---|---|---|---|---|
| February 2016 (n = 9) | | | | | |
| 'Florida Brilliance' | 6.7 a | 4.8 a | 5.2 a | 3.3 a | 2.3 a |
| 'Florida127' | 4.7 b | 5.2 a | 4.8 a | 4.1 a | 2.1 a |
| 'Florida Radiance' | 4.0 b | 4.8 a | 5.4 a | 4.1 a | 2.2 a |

TABLE 2-continued

Trained sensory panel ratings from five dates over two harvest seasons.

| Cultivar | Firm-ness | Sweet-ness | Sour-ness | Strawberry flavor | Green flavor |
|---|---|---|---|---|---|
| March 2016 (n = 9) | | | | | |
| 'Florida Brilliance' | 7.1 a | 2.7 b | 4.9 b | 1.7 b | 3.6 ab |
| 'Florida127' | 5.4 b | 4.7 a | 5.0 b | 3.6 a | 2.0 b |
| 'Florida Radiance' | 5.9 b | 2.8 b | 6.9 a | 2.0 b | 4.0 a |
| January 2017 (n = 12) | | | | | |
| 'Florida Brilliance' | 6.4 a | 3.5 a | 5.1 a | 2.9 a | 3.0 a |
| 'Florida127' | 5.8 b | 3.8 a | 5.2 a | 3.4 a | 2.2 b |
| 'Florida Radiance' | 5.3 b | 3.6 a | 4.8 a | 3.1 a | 2.0 b |
| February 2017 (n = 10) | | | | | |
| 'Florida Brilliance' | 4.6 a | 3.4 b | 5.0 a | 3.2 a | 2.4 a |
| 'Florida127' | 4.4 a | 4.5 a | 4.4 a | 3.7 a | 1.5 a |
| 'Florida Radiance' | 3.9 a | 2.8 b | 4.8 a | 2.4 a | 1.9 a |

TABLE 2-continued

Trained sensory panel ratings from five dates over two harvest seasons.

| Cultivar | Firm-ness | Sweet-ness | Sour-ness | Strawberry flavor | Green flavor |
|---|---|---|---|---|---|
| March 2017 (n = 10) | | | | | |
| 'Florida Brilliance' | 6.2 a | 3.8 b | 4.9 a | 3.1 b | 1.5 a |
| 'Florida127' | 5.5 ab | 5.2 a | 4.2 a | 4.5 a | 1.1 a |
| 'Florida Radiance' | 4.7 b | 3.5 b | 4.8 a | 2.9 b | 1.9 a |

Mean separations are within harvest dates and within columns by Fisher's LSD test, $P \leq 0.05$. Different letters within harvest date and within column indicate comparisons that achieved statistical significance.

What is claimed is:

1. A new and distinct strawberry plant named 'Florida Brilliance' as illustrated and described herein.

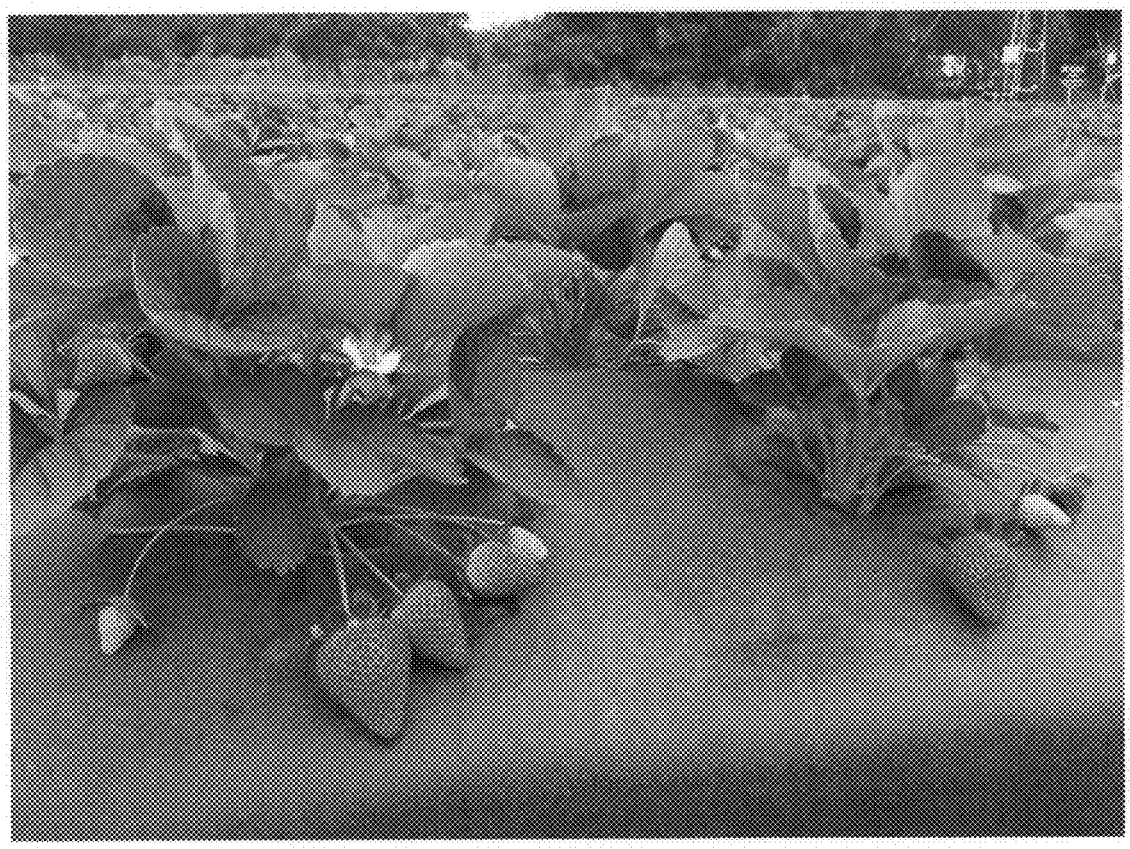

* * * * *